$$\text{US010888614B2}$$

United States Patent
Ondei et al.

(10) Patent No.: US 10,888,614 B2
(45) Date of Patent: Jan. 12, 2021

(54) EMULSIONS FOR INJECTABLE FORMULATIONS

(71) Applicant: CRODA INTERNATIONAL PLC, Yorkshire (GB)

(72) Inventors: Roberta Ondei, Campinas-São Paulo (BR); Edna Fernandes, Campinas-São Paulo (BR)

(73) Assignee: Croda International Plc

( * ) Notice: Subject to any disclaimer, the term of this patent is extended or adjusted under 35 U.S.C. 154(b) by 210 days.

(21) Appl. No.: 15/565,983

(22) PCT Filed: Apr. 4, 2016

(86) PCT No.: PCT/GB2016/050952
§ 371 (c)(1),
(2) Date: Oct. 12, 2017

(87) PCT Pub. No.: WO2016/170302
PCT Pub. Date: Oct. 27, 2016

(65) Prior Publication Data
US 2018/0104329 A1    Apr. 19, 2018

(30) Foreign Application Priority Data
Apr. 23, 2015    (GB) .................................. 1506948.7

(51) Int. Cl.
*A61K 39/39* (2006.01)
*A61K 9/107* (2006.01)
*A61K 47/10* (2017.01)
*A61K 47/12* (2006.01)
*A61K 47/44* (2017.01)
*A61K 47/18* (2017.01)
*A61K 39/00* (2006.01)

(52) U.S. Cl.
CPC .............. *A61K 39/39* (2013.01); *A61K 9/107* (2013.01); *A61K 47/10* (2013.01); *A61K 47/12* (2013.01); *A61K 47/18* (2013.01); *A61K 47/44* (2013.01); *A61K 2039/55566* (2013.01)

(58) Field of Classification Search
CPC ................... A61K 39/39; A61K 9/107; A61K 2039/55566
See application file for complete search history.

(56) References Cited

U.S. PATENT DOCUMENTS

| | | | | |
|---|---|---|---|---|
| 5,422,109 A | * | 6/1995 | Brancq | A61K 9/0019 424/184.1 |
| 8,496,939 B2 | | 7/2013 | Jansen et al. | |
| 2006/0034937 A1 | | 2/2006 | Patel | |
| 2009/0017067 A1 | * | 1/2009 | Diehl | A61K 39/145 424/209.1 |
| 2010/0143462 A1 | * | 6/2010 | Garti | A61K 9/1075 424/455 |
| 2012/0141585 A1 | | 6/2012 | Coulter et al. | |

FOREIGN PATENT DOCUMENTS

| | | |
|---|---|---|
| EP | 1367997 B1 | 8/2009 |
| WO | 02067899 A1 | 9/2002 |
| WO | 02089762 A1 | 11/2002 |
| WO | 2011116049 A1 | 9/2011 |

OTHER PUBLICATIONS

Atlox™ Polymeric Surfactants—1 page.
International Search Report and Written Opinion for International Application No. PCT/GB2016/050952, dated May 13, 2016—9 Pages.
"Stable Emulsion Formulation Using the Combination of Polyakylene Glycol Ether and Alkyd-Poylethylene Glycol Resin Polymeric Surfactants", disclosed by Croda, www.researchdisclosure.com, published digitally on Aug. 2, 2013—6 pages.
Strickley, R., "Solubilizing Excipients in Oral and Injectable Formulations", Pharmaceutical Research, vol. 21, No. 2, Feb. 2004, pp. 201-230.
Colombian Office Action for Colombia Application No. NC2017/0010659, dated Sep. 27, 2018, 17 pages.

* cited by examiner

*Primary Examiner* — Jianfeng Song
(74) *Attorney, Agent, or Firm* — RatnerPrestia

(57) ABSTRACT

Emulsifiers for emulsions vaccine formulations and use in water-in-oil emulsion for vaccine formulations as an emulsifier. The emulsifier is an alkoxylated polyol or polyamine which is optionally acyl terminated. There is also provided a method of forming the vaccine formulation. The emulsifiers provide for emulsions which may require less emulsifier than known emulsifiers, and provide stable emulsions.

10 Claims, No Drawings

EMULSIONS FOR INJECTABLE FORMULATIONS

CROSS REFERENCE TO RELATED APPLICATIONS

This application is the National Stage filing of International Appln. No. PCT/GB2016/050952, filed Apr. 4, 2016, and claims priority of GB Application No. 1506948.7, filed Apr. 23, 2015, the entirety of which applications is incorporated herein by reference for all purposes.

The present invention relates to emulsifiers for injectable water-in-oil emulsions, and in particular for use of said emulsions in formulations for veterinary vaccines. The present invention also includes methods of preparing said formulations.

Water-in-oil (w/o) emulsions are two phase systems consisting of an oil phase (continuous phase) and an aqueous phase (discontinuous phase). The aqueous phase is dispersed as small droplets in the oil phase, and the emulsion contains one or more surfactants and emulsifiers. Water-in-oil emulsions are widely applied in medicine, cosmetics, and the food and beverage industry. In medicine water-in-oil emulsions are generally used in pharmaceutical formulations as vehicle for delivery of active agents, especially in case of water-insoluble or water-sensitive active agents.

In vaccinations, water-in-oil emulsions are commonly used as an adjuvant to stimulate the immune response against target antigens derived from one or more infectious agents. These water-in-oil emulsions are generally applied via injection. To be injectable a composition must be substantially fluid. However these types of water-in-oil emulsions are often relatively viscous which makes injection of them problematic.

One way to try and overcome this problem is to use different oils in the emulsion selected from both mineral and non-mineral (metabolisable) oils. However, although oil based adjuvants generally increase the immunological activity of the vaccines, compared to non-oily vaccines, they can cause local reactions at the injection site especially when mineral oils are used.

Metabolisable oils, and in particular (semi-) synthetic- and vegetable oils are viscous at room temperature and their use in w/o emulsions leads to emulsion viscosity values that are similar to that of the individual oil. A reduction of the oil content (and consequently an increase in the water content) often causes an increase in the emulsion viscosity to such an extent that injection is no longer possible. Reduction of the oil content results in an enlarged interfacial area and the amount of emulsifier will be insufficient and the emulsion will break. In addition, changes in the oil content of a w/o emulsion effect the stability of the emulsion.

These limitations make it difficult to obtain stable and fluid w/o emulsions, especially when based on metabolisable oils. Hence there is a need to find other methods and/or means to obtain stable w/o emulsions, which at the same time are fluid. The present invention aims to provide emulsifiers and stable w/o emulsions with an acceptable shelf life that are very suitable for including in formulations for injection, and which have desired viscosity.

Therefore, there is a need for emulsifiers for water-in-oil emulsions for used in vaccine formulations which are able to provide comparable or improved properties compared to existing emulsifiers.

According to a first aspect of the present invention there is provided a vaccine formulation comprising a water-in-oil emulsion and at least one vaccine antigen, oil, and water, where said emulsion comprises an emulsifier being an alkoxylated polyol or polyamine which is optionally acyl terminated.

According to a second aspect of the present invention there is provided a method of forming vaccine formulation which comprises mixing together:
(i) at least one emulsifier, said emulsifier being an alkoxylated polyol or polyamine which is optionally acyl terminated;
(ii) at least one vaccine antigen;
(iii) oil; and
(iv) water.

According to a third aspect of the present invention there is provided the use of an alkoxylated polyol or polyamine which is optionally acyl terminated as an emulsifier in a water-in-oil emulsion for vaccine formulations.

According to a fourth aspect of the present invention there is provided a water-in-oil emulsion comprising emulsifier being an alkoxylated polyol or polyamine which is optionally acyl terminated, said emulsifier being present in the emulsion in the range from 0.1 wt. % to 10 wt. %.

According to a fifth aspect of the present invention there is provided an oil phase comprising oil and a emulsifier being an alkoxylated polyol or polyamine which is optionally acyl terminated, said oil phase suitable for forming a an emulsion according to the fourth aspect and/or a vaccine formulation according to the first aspect.

It has been found that use of an optionally acyl terminated alkoxylated polyol or polyamine as an emulsifier for a water-in-oil emulsion provides for emulsions particularly suitable for injectable vaccine formulations. The emulsifiers provide for emulsions which may require less emulsifier than known emulsifiers, and continue to provide stable emulsions.

As used herein, the terms 'for example,' 'for instance,' 'such as,' or 'including' are meant to introduce examples that further clarify more general subject matter. Unless otherwise specified, these examples are provided only as an aid for understanding the applications illustrated in the present disclosure, and are not meant to be limiting in any fashion.

It will be understood that, when describing the number of carbon atoms in a substituent group (e.g. '$C_1$ to $C_6$ alkyl'), the number refers to the total number of carbon atoms present in the substituent group, including any present in any branch groups. Additionally, when describing the number of carbon atoms in, for example fatty acids, this refers to the total number of carbon atoms including the one at the carboxylic acid, and any present in any branch groups.

The emulsifier is an alkoxylated polyol or polyamine which is optionally acyl terminated, and may have a general structure (I):

$$R^1\text{-}[(AO)_n\text{---}R^2]_m \hspace{2cm} (I)$$

wherein
$R^1$ is the residue of a polyol or polyamine, each said polyol or polyamine having m active hydrogen atoms, where m is an integer of at least 2;
AO is an oxyalkylene group;
each n independently represents an integer in the range from 1 to 100;
each $R^2$ is independently represents hydrogen, or an acyl group represented by —$C(O)R^3$ wherein each $R^3$ independently represents a residue of polyhydroxyalkyl carboxylic acid, polyhydroxyalkenyl carboxylic acid, hydroxyalkyl carboxylic acid, hydroxyalkenyl carboxylic acid, oligomer of hydroxyalkyl carboxylic acid, or oligomer of hydroxyalkenyl carboxylic acid; and wherein on average at least two $R^2$ groups per molecule are alkanoyl groups as defined.

The compounds of the present invention are at least notionally built up from the group $R^1$ that can be considered as the "core group" of the compounds. This core group is the residue (after removal of m active hydrogen atoms) of a compound containing at least m active hydrogen atoms, preferably present in hydroxyl and/or amino groups, and more preferably present in hydroxyl groups only.

The term polyol is well known in the art, and refers to an alcohol comprising more than one hydroxyl group. The term 'active hydrogen' refers to the hydrogen atoms present as part of the hydroxyl groups of the polyol. Therefore, it will be understood that the integer m, being the number of active hydrogens in said polyol, is equivalent to the number of hydroxyl groups present for each polyol.

The term 'polyol residue' as used herein, unless otherwise defined, refers to an organic radical derived from polyol by removal of m active hydrogen atoms, each hydrogen atom being from one of the hydroxyl groups present.

The term polyamine will also be similarly understood, although will have amino groups in place of hydroxyl groups.

Preferably the core group is the residue of an amino and/or hydroxyl comprising hydrocarbyl, particularly a $C_3$ to $C_{30}$ amino and/or hydroxyl comprising hydrocarbyl.

Examples of $R^1$ core groups include the residues of the following compounds after removal of m active hydrogen atoms:

glycerol and the polyglycerols, especially diglycerol and triglycerol, the partial esters thereof, or any triglycerides containing multiple hydroxyl groups, for example castor oil;
  tri- and higher polymethylol alkanes such as trimethylol ethane, trimethylol propane and pentaerythritol, and the partial esters thereof;
  sugars, particularly non-reducing sugars such as sorbitol, mannitol, and lactitol, etherified derivatives of sugars such as sorbitan (the cyclic dehydro-ethers of sorbitol), partial alkyl acetals of sugars such as methyl glucose and alkyl;
  (poly-)saccharides, and other oligo-/poly-mers of sugars such as dextrins, partially esterified derivatives of sugars, such as fatty acid esters, for example of lauric, palmitic, oleic, stearic and behenic acid, esters of sorbitan, sorbitol, and sucrose, aminosaccharides such as N-alkylglucamines and their respective N-alkyl-N-alkenoyl glucamides;
  polyhydroxy carboxylic acids especially citric and tartaric acids;
  amines including di- and poly-functional amines, particularly alkylamines including alkyl diamines such as ethylene diamine (1,2-diaminoethane);
  amino-alcohols, particularly the ethanolamines, 2-aminoethanol, di-ethanolamine and triethanolamine;
  carboxylic acid amides such as urea, malonamide and succinamide; and
  amido carboxylic acids such as succinamic acid.

Preferred $R^1$ core groups are residues of groups having at least 3, more preferably in the range from 4 to 10, particularly 5 to 8, and especially 6 free hydroxyl and/or amino groups.

The $R^1$ group preferably has a linear $C_4$ to $C_7$, more preferably $C_6$ chain. The hydroxyl or amino groups are preferably directly bonded to the chain carbon atoms. Hydroxyl groups are preferred. $R^1$ is preferably the residue of an open chain tetratol, pentitol, hexitol or heptitol group or an anhydro e.g. cycloether anhydro, derivative of such a group. In a particularly preferred embodiment, $R^1$ is the residue of, or a residue derived from, a sugar, more preferably a monosaccharide such as glucose, fructose or sorbitol, a disaccharide such as maltose, palitose, lactitol or lactose or a higher oligosaccharide. $R^1$ is preferably the residue of a monosaccharide, more preferably of glucose, fructose or sorbitol, and particularly of sorbitol.

The open chain form of $R^1$ groups is preferred; however groups including internal cyclic ether functionality can be used, and may be obtained inadvertently if the synthetic route exposes the group to relatively high temperatures or other conditions, which promote such cyclisation.

The index m is a measure of the functionality of the $R^1$ core group and the alkoxylation reactions will replace some or all of the active hydrogen atoms (dependant on the molar ratio of core group to alkoxylation group) in the molecule from which the core group is derived. Reaction at a particular site may be restricted or prevented by steric hindrance or suitable protection. The terminating hydroxyl groups of the polyalkylene oxide chains in the resulting compounds are then available for reaction with the above defined acyl compounds.

The index m will preferably be at least 3, more preferably in the range from 4 to 10, particularly 5 to 8, and especially 5 to 6. Mixtures may be, and normally are, employed, and therefore m when specified across a bulk amount of the emulsifier, can be an average value and may be non-integral.

The groups $R^2$ are the "terminating groups" of the (poly) alkylene oxide chains. The terminating groups are hydrogen or an acyl (also known as alkanoyl) group represented by —C(O)$R^3$, where each $R^3$ independently represents a residue of polyhydroxyalkyl carboxylic acid, polyhydroxyalkenyl carboxylic acid, hydroxyalkyl carboxylic acid, hydroxyalkenyl carboxylic acid, oligomer of hydroxyalkyl carboxylic acid, or oligomer of hydroxyalkenyl carboxylic acid The hydroxylalkyl and hydroxyalkenyl carboxylic acids are of formula HO—X—COOH where X is a divalent saturated or unsaturated, preferably saturated, aliphatic radical containing at least 8 carbon atoms and no more than 20 carbon atoms, typically from 11 to 17 carbons and in which there are at least 4 carbon atoms directly between the hydroxyl and carboxylic acid groups.

Desirably the hydroxyalkyl carboxylic acid is 12-hydroxystearic acid. In practice such hydroxyalkyl carboxylic acids are commercially available as mixtures of the hydroxyl acid and the corresponding unsubstituted fatty acid. For example 12-hydroxystearic acid is typically manufactured by hydrogenation of castor oil fatty acids including the $C_{18}$ unsaturated hydroxyl acid and the non-substituted fatty acids (oleic and linoleic acids) which on hydrogenation gives a mixture of 12-hydroxystearic and stearic acids. Commercially available 12-hydroxystearic acid typically contains about 5 to 8% unsubstituted stearic acid.

The polyhydroxyalkyl or polyhydroxyalkenyl carboxylic acid is manufactured by polymerising the above mentioned hydroxyalkyl or hydroxyalkenyl carboxylic acid. The presence of the corresponding unsubstituted fatty acid acts as a terminating agent and therefore limits the chain length of the polymer. Desirably the number of hydroxyalkyl or hydroxyalkenyl units is on average from 2 to 10, particularly from about 4 to 8 and especially about 7. The molecular weight of the polyacid is typically from 600 to 3,000, particularly from 900 to 2,700, more particularly from 1,500 to 2,400 and especially about 2,100.

The residual acid value for the polyhydroxyalkyl or polyhydroxyalkenyl carboxylic acid typically is less than 50 mgKOH/g, and a preferable range is 30 to 35 mgKOH/g. Typically, the hydroxyl value for the polyhydroxyalkyl or polyhydroxyalkenyl carboxylic acid is a maximum of 40 mgKOH/g, and a preferable range is 20 to 30 mgKOH/g.

The oligomer of the hydroxyalkyl or hydroxyalkenyl carboxylic acid differs from the polymer in that termination is not by the unsubstituted corresponding fatty acid. Desirably it is a dimer of the hydroxylalkyl or hydroxyalkenyl carboxylic acid.

The oxyalkylene groups (AO) may be selected from groups of the formula —($C_yH_{2y}O$)— where y is an integer selected from 2, 3, or 4. Preferably, y is 2 or 3.

The oxyalkylene group AO may be selected from oxyethylene, oxypropylene, oxybutylene, or oxytetramethylene. Preferably, the oxyalkylene group is selected from oxyethylene (EO) and/or oxypropylene (PO).

Where the oxyalkylene chain is homopolymeric, homopolymers of ethylene oxide or propylene oxide are preferred. More preferably, homopolymers of ethylene oxide are particularly preferred.

Where there is more than one oxyalkylene group present (i.e. where n is 2 or more) and at least two are part of the same oxyalkylene chain, the oxyalkylene groups may be the same or may be different along said oxyalkylene chain. In this embodiment, the oxyalkylene chain may be a block or random copolymer of differing oxyalkylene groups.

Usually, where co-polymeric chains of ethylene and propylene oxide units are used the molar proportion of ethylene oxide units used will be at least 50% and more usually at least 70%.

The number of alkylene oxide residues in the (poly) alkylene oxide chains, i.e. the value of the each parameter n, will preferably be in the range from 2 to 50, more preferably 3 to 20, and particularly 5 to 10.

The total of the indices n (i.e. n×m) is preferably in the range from 10 to 300, more preferably 20 to 100, particularly 25 to 70, and especially 30 to 50.

Where the number of acyl residues in the molecule is significantly less than m, the distribution of such groups may depend on the nature of the core group and on the extent and effect of the alkoxylation of the core group. Thus, where the core group is derived from pentaerythritol, alkoxylation of the core residue may be evenly distributed over the four available sites from which an active hydrogen can be removed and on esterification of the terminal hydroxyl functions the distribution of acyl groups will be close to the expected random distribution. However, where the core group is derived from compounds, such as sorbitol, where the active hydrogen atoms are not equivalent, alkoxylation will typically give unequal chain lengths for the polyalkyleneoxy chains. This may result in some chains being so short that the other (longer) chains exert significant steric effects making esterification at the "short chain" terminal hydroxyl groups relatively difficult. Esterification then will generally preferentially take place at the "long chain" terminal hydroxyl groups.

The emulsifier of the invention can be made by firstly alkoxylating $R^1$ core groups containing m active hydrogen atoms, by techniques well known in the art, for example by reacting with the required amounts of alkylene oxide, for example ethylene oxide and/or propylene oxide. Some suitable alkoxylated products are commercially available, for example sorbitol 30 ethoxylate (Atlas™ G-2330), sorbitol 40 ethoxylate (Atlas™ G-2004), sorbitol 50 ethoxylate (Atlas™ G-2005), and trimethylolpropane 40 ethoxylate propoxylate (Emkarox™ VG-305W). All are available ex Croda. Other alkoxylation products include sorbitol 12 ethoxylate and sorbitol 100 ethoxylate.

The second stage of the process preferably comprises reacting the aforementioned alkoxylated species with a polyhydroxyalkyl (alkenyl) carboxylic acid and/or a hydroxyalkyl(alkenyl) carboxylic acid under standard catalysed esterification conditions at temperatures up to 250° C.

The molar ratio of alkoxylated product to a polyhydroxyalkyl (alkenyl) carboxylic acid and/or a hydroxyalkyl(alkenyl) carboxylic acid preferably ranges from 1:2 to 1:40.

The emulsifier is a liquid with a molecular weight ranging from 3,000 to 8,000. The emulsifier is preferably a star block copolymer.

One of the key benefits of the emulsifier is that it can have a wide range of HLB depending on whether the $R^3$ group is a residue of a polyhydroxyalkylcarboxylic acid, a hydroxyl alkylcarboxylic acid, an oligomer of a hydroxyalkyl carboxylic acid, or a mixture thereof and also depending on the ratio of each of these ingredients. The typical range of HLB is from 1.3 to 15.0.

In one preferred embodiment of the invention the emulsifier is prepared by reaction of the alkoxylated core group $R^1$ with a hydroxyl alkylcarboxylic acid in a molar ratio of from 1:14 to 1:19. Preferably the emulsifier prepared by this route has an HLB of between 6 and 9 and a molecular weight between 6,500 and 8,000.

In a further preferred embodiment of the invention the emulsifier is prepared by reaction of the alkoxylated core group $R^1$ with a mixture of a polyhydroxyalkyl carboxylic acid and a hydroxyl alkylcarboxylic acid where the molar ratio of alkoxylated core group to mixture of acids. Preferably the molar ratio of alkoxylated core group to mixture of acids ranges from 1:1 to 1:6. Preferably the emulsifier prepared by this route has an HLB of between 12 and 15 and a molecular weight between 3,000 and 4,000.

In a further preferred embodiment of the invention the emulsifier is prepared by reaction of the alkoxylated core group $R^1$ with a polyhydroxyalkyl carboxylic acid where the molar ratio of alkoxylated core group to acid preferably ranges from 1:14 to 1:19. Preferably the emulsifier prepared by this route has an HLB of between 6 and 9 and a molecular weight between 6,500 and 8,000.

The emulsifier as used in water based systems is generally water soluble, having an HLB greater than 7.

The concentration of the oil in the water in oil emulsion may vary, and the amount of oil is typically from 1 wt. % to 90 wt. %, usually 10 wt. % to 80 wt. %, more usually 20 wt. % to 70 wt. %, particularly 30 wt. % to 60 wt. %, and especially 40 wt. % to 55 wt. % by weight of the total emulsion.

The amount of water present in the emulsion is typically greater than 5 wt. %, usually from 10 wt. % to 90 wt. %, more usually 25 wt. % to 75 wt. %, particularly 35 wt. % to 65 wt. %, and especially 45 wt. % to 55 wt. % by weight of the total composition.

The water in oil emulsion according to the invention may comprise 0.1 wt. % to 15 wt. %, preferably 0.4 wt. % to 10 wt. %, more preferably 0.7 wt. % to 5 wt. %, most preferably 0.9 wt. % to 3 wt. % of the emulsifier according to the invention. The amount of emulsifier present in the emulsion may most preferably in the range from 1.0 wt. % to 2.0 wt. %. A particular advantage of the present invention is that the amount of emulsifier required in order to provide desired emulsification of the emulsion may be particularly low when compared to prior emulsifiers in the art.

In a preferred embodiment, a water in oil emulsion according to the invention comprises 1.5 wt. % of the emulsifier.

The emulsifier of the present invention was found to be compatible with a wide variety of oils, thus providing a much wider range of water in oil emulsions having the required stability and fluidity to ensure administration by injection. The use of the present emulsifiers provided water in oil emulsions having good stability during storage thus improving the shelf life of said emulsions. The emulsions were found to be stable and fluid at low temperatures, especially at 25° C.

Other emulsifiers may also be used in the water in oil emulsion in addition to the emulsifier of the present invention.

In one embodiment of the invention the water-in-oil emulsion consists essential of an emulsifier being an alkoxylated polyol or polyamine which is optionally acyl terminated, water, and oil. The emulsion may consist essentially of these components, or contain said components with no other components present in the emulsion.

Suitable oils for use in the water in oil emulsion according to the present invention are non-metabolisable oils, metabolisable oils, and mixtures of metabolisable and non-metabolisable oils.

Non metabolisable oils that may be used in the adjuvants according to the invention include but are not limited to mineral oils and paraffin oils. Mineral oils may be preferred.

Metabolisable oils include, but are not limited to, vegetable oils, animal oils, natural hydrocarbons, metabolisable synthetic or semi-synthetic oils (such as Miglyol and Cetiol), fatty acid esters of propylene glycol and $C_6$ to $C_{24}$ fatty acids such as oleyl oleates, diesters of capric- or caprylic acids and the like. Suitable vegetable oils are peanut oil, soybean oil, sunflower oil, and the like. Suitable animal oils are squalane and squalene and the like.

The oil phase may be metabolisable oil or a mixture of metabolisable oils, since non-metabolisable oils (mineral oils) may give local reactions at the injection sites.

The water in oil emulsions according to the invention can be prepared using standard techniques. In general the aqueous phase, the oil phase, the emulsifier, and optionally other emulsifiers and components are brought together and emulsified until a stable emulsion having the desired low viscosity is obtained.

When emulsions are prepared, energy must be expended to form an interface between the oily and aqueous phases. Therefore, emulsification equipment includes a wide variety of agitators, homogenisers, colloid mills, jet mixers and ultrasonic devices. Production-size agitators can be propeller shaped or paddle shaped stirring systems, with rotation speed usually up to 2,000 rpm, and are considered as low shear mixing procedures. Another type of production-site agitator is the colloid mill. The principle of operation of the colloid mill is the passage of the mixed phases of an emulsion formula between a stator and a high-speed rotor revolving at speeds of 2,000 to 18,000 rpm that is considered as a high shear mixing procedure.

The emulsifier according to the invention is preferably present in the oil phase. Additional emulsifiers may be incorporated in the aqueous phase or oil phase.

Water-in-oil emulsions of the present invention can be processed into a water-in-oil-in-water emulsion (also called "double emulsions"), where the internal and external aqueous phases are separated by an oil phase. This process consists of mixing the water-in-oil emulsion into an aqueous phase containing the emulsifier of the present invention. Therefore, it should be understood that these water-in-oil-in-water emulsions are included within the scope of water-in-oil emulsions as defined herein.

In case of a water-in-oil-in-water emulsion, a water in oil emulsion according to the invention is prepared as primary water in oil emulsion, which is subsequently added to a second aqueous phase and a second emulsifier and homogenised to obtain the desired water-in-oil-in-water emulsion. The second emulsifier required to make the water-in-oil-in-water emulsion is preferably an emulsifier with an HLB of 10-18, or a combination of two or more emulsifiers so that a desired HLB is obtained.

The water-in-oil and water-in-oil-in-water emulsions according to the present invention are suitable for use in vaccine formulations.

The emulsifiers of the present invention provide for desired stability of the resulting emulsion. The emulsions do not undergo significant separation under storage, in particular at the bottom of the container. Separation under storage is considered critical as breakage is a critical default.

The emulsion of the present invention, have a maximum separation of 15% and preferably not more than 10% at an accelerated test over 15 days at 37° C. where the separation is as defined in the Examples and the emulsifier is present at 1.5 wt. %. Most preferably, the emulsion has no more than 6% separation for an accelerated test over 15 days at 37° C.

The emulsion of the present invention, have a maximum separation of 15% and preferably not more than 10% at a test over 3 months at 5-8° C. where the separation is as defined in the Examples and the emulsifier is present at 1.5 wt. %. Most preferably, the emulsion has no more than 6% separation over 3 months at 5-8° C.

It will be understood that viscosity values defined below are based on emulsions with 1.5 wt. % emulsifier as shown in the Examples. Methods of determining zero-shear viscosity are as described in more detail herein. Zero-shear viscosity will be understood to represent the viscosity at the limit of low shear rate, i.e. the maximum plateau value attained as shear stress or shear rate is reduced, and is effectively the viscosity of the composition whilst at rest.

The zero-shear viscosity of the emulsion at 0 days may be less than 130 cP. The viscosity may be in the range from 30 to 110 cP. Preferably, the zero-shear viscosity is in the range from 50 to 95 cP. More preferably, the zero-shear viscosity is in the range from 65 to 85 cP.

It will be understood that the phrase 0 days refers to measurements made just after the emulsion is formed.

The zero-shear viscosity of the emulsion at 15 days and 37° C. may be less than 130 cP. The viscosity may be in the range from 35 to 110 cP. Preferably, the zero-shear viscosity is in the range from 50 to 95 cP. More preferably, the zero-shear viscosity is in the range from 65 to 85 cP.

The zero-shear viscosity of the emulsion at 1 month and 5-8° C. may be less than 130 cP. The viscosity may be in the range from 20 to 110 cP. Preferably, the zero-shear viscosity is in the range from 55 to 100 cP. More preferably, the zero-shear viscosity is in the range from 70 to 90 cP.

The zero-shear viscosity of the emulsion at 2 months and 5-8° C. may be less than 130 cP. The viscosity may be in the range from 20 to 120 cP. Preferably, the zero-shear viscosity is in the range from 60 to 110 cP. More preferably, the zero-shear viscosity is in the range from 75 to 98 cP.

The zero-shear viscosity of the emulsion at 3 months and 5-8° C. may be less than 130 cP. The viscosity may be in the range from 20 to 110 cP. Preferably, the zero-shear viscosity is in the range from 55 to 100 cP. More preferably, the zero-shear viscosity is in the range from 70 to 90 cP.

The emulsion of the present invention therefore provides good viscosity in a range desirable for syringeability at low concentration of the emulsifier. In addition, the emulsions of the present invention maintain the desired viscosity under storage over time.

The emulsions of the present invention, have a change in viscosity when not under shear (zero-shear) between 0 hours and 15 days when kept at 37° C. of no more than 20%, preferably no more than 15%, most preferably no more than 10%.

The emulsions of the present invention, have a change in viscosity when not under shear (zero-shear) between 0 hours and 2 months when kept at 5-8° C. of no more than 30%, preferably no more than 20%, most preferably no more than 15%.

The emulsions of the present invention, have a change in viscosity when not under shear (zero-shear) between 0 hours and 3 months when kept at 5-8° C. of no more than 30%, preferably no more than 20%, most preferably no more than 15%.

In relation to the emulsion and emulsifier, it has been found that the listed viscosity ranges provide for the desired viscosity of the emulsion and for the vaccine formulation formed with said emulsion. In particular, these desired viscosity ranges are obtained even with low amounts of the emulsifier being present in the emulsion as described herein.

It will be appreciated that the emulsion comprises particles of water and therefore the particle size and distribution is a factor which reflects the stability of the emulsion. It is important that there is a homogeneous distribution of the particles to ensure stability of the emulsion for a longer period. Additionally, an effective emulsifier ensures that the particles do not come together and cause phase separation. Therefore, an emulsion with small particle size and homogeneous particle distribution is likely to be a more stable emulsion.

In the form of a distribution of particle sizes, the particles would have a median volume particle diameter value. It will be understood that the median volume particle diameter refers to the equivalent spherical diameter corresponding to the point on the distribution which divides the population exactly into two equal halves. It is the point which corresponds to 50% of the volume of all the particles, read on the cumulative distribution curve relating volume percentage to the diameter of the particles i.e. 50% of the distribution is above this value and 50% is below. This value is referred to as the "D(v,0.5)" value and is determined as described herein.

Additionally, "D(v,0.9)" and "D(v,0.1)" values can also be referred to, and these values would be the equivalent spherical diameter corresponding to 90% or 10% respectively of the volume of all the particles, read on the cumulative distribution curve relating volume percentage to the diameter of the particles, i.e. they are the points where 10% or 90% of the distribution is above this value and 90% or 10% are below the value respectively.

The particle size values, used to determine the D(v,0.5), D(v,0.1), and D(v,0.9) values, are measured by techniques and methods as described in further detail herein. It will be understood that particle size values defined below are based on emulsions with 1.5 wt. % emulsifier as shown in the Examples.

It is generally known that particle sizes are particularly relevant to long term stability of the emulsion. In particular, the lower the size of D(v,0.9) the higher the stability of the formulation over a longer period of stability, and generally particle sizes in the range 1-10 μm are preferred in order to obtain an emulsion having the desired properties. Additionally, monomodal particle size distribution over time is an indication of emulsion stability.

The particles present in emulsions of the present invention may have a D(v,0.5) value at 0 days in the range from 0.7 μm to 7.0 μm. Preferably, in the range from 1.0 μm to 5.0 μm. More preferably, in the range from 1.2 μm to 3.0 μm. Most preferably, in the range from 1.5 μm to 2.1 μm.

The particles present in emulsions of the present invention may have a D(v,0.1) value at 0 days in the range from 0.5 μm to 7.0 μm. Preferably, in the range from 0.7 μm to 4.0 μm. More preferably, in the range from 0.8 μm to 2.0 μm. Most preferably, in the range from 0.9 μm to 1.3 μm.

The particles present in emulsions of the present invention may have a D(v,0.9) value at 0 days in the range from 0.5 μm to 10.0 μm. Preferably, in the range from 0.7 μm to 7.0 μm. More preferably, in the range from 1.0 μm to 4.0 μm. Most preferably, in the range from 2.4 μm to 3 μm.

The particles present in emulsions of the present invention may have a D(v,0.5) value at 15 days and 37° C. in the range from 0.7 μm to 8.0 μm. Preferably, in the range from 1.0 μm to 5.0 μm. More preferably, in the range from 1.2 μm to 3.0 μm. Most preferably, in the range from 1.5 μm to 2.1 μm.

The particles present in emulsions of the present invention may have a D(v,0.1) value at 15 days and 37° C. in the range from 0.5 μm to 7.0 μm. Preferably, in the range from 0.7 μm to 4.0 μm. More preferably, in the range from 0.8 μm to 2.0 μm. Most preferably, in the range from 0.9 μm to 1.3 μm.

The particles present in emulsions of the present invention may have a D(v,0.9) value at 15 days and 37° C. in the range from 0.5 μm to 10.0 μm. Preferably, in the range from 0.7 μm to 7.0 μm. More preferably, in the range from 1.0 μm to 4.0 μm. Most preferably, in the range from 2.4 μm to 3.1 μm.

The particles present in emulsions of the present invention may have a D(v,0.5) value at 1 month at 5-8° C. in the range from 0.7 μm to 8.0 μm. Preferably, in the range from 1.0 μm to 5.0 μm. More preferably, in the range from 1.2 μm to 3.0 μm. Most preferably, in the range from 1.5 μm to 2.1 μm.

The particles present in emulsions of the present invention may have a D(v,0.1) value at 1 month at 5-8° C. in the range from 0.5 μm to 7.0 μm. Preferably, in the range from 0.7 μm to 4.0 μm. More preferably, in the range from 0.8 μm to 2.0 μm. Most preferably, in the range from 1.0 μm to 1.3 μm.

The particles present in emulsions of the present invention may have a D(v,0.9) value at 1 month at 5-8° C. in the range from 0.5 μm to 10.0 μm. Preferably, in the range from 0.7 μm to 7.0 μm. More preferably, in the range from 1.0 μm to 4.0 μm. Most preferably, in the range from 2.4 μm to 3.1 μm.

The particles present in emulsions of the present invention may have a D(v,0.5) value at 2 months at 5-8° C. in the range from 0.7 μm to 8.0 μm. Preferably, in the range from 1.0 μm to 5.0 μm. More preferably, in the range from 1.2 μm to 3.0 μm. Most preferably, in the range from 1.5 μm to 2.1 μm.

The particles present in emulsions of the present invention may have a D(v,0.1) value at 2 months at 5-8° C. in the range from 0.5 μm to 7.0 μm. Preferably, in the range from 0.7 μm to 4.0 μm. More preferably, in the range from 0.8 μm to 2.0 μm. Most preferably, in the range from 0.9 μm to 1.3 μm.

The particles present in emulsions of the present invention may have a D(v,0.9) value at 2 months at 5-8° C. in the range from 0.5 μm to 10.0 μm. Preferably, in the range from 0.7 μm to 7.0 μm. More preferably, in the range from 1.0 μm to 4.0 μm. Most preferably, in the range from 2.4 μm to 3.1 μm.

The particles present in emulsions of the present invention may have a D(v,0.5) value at 3 months at 5-8° C. in the range from 0.7 μm to 8.0 μm. Preferably, in the range from 1.0 μm to 5.0 μm. More preferably, in the range from 1.2 μm to 3.0 μm. Most preferably, in the range from 1.5 μm to 2.1 μm.

The particles present in emulsions of the present invention may have a D(v,0.1) value at 3 months at 5-8° C. in the range from 0.5 μm to 7.0 μm. Preferably, in the range from 0.7 μm to 4.0 μm. More preferably, in the range from 0.8 μm to 1.8 μm. Most preferably, in the range from 0.85 μm to 1.1 μm.

The particles present in emulsions of the present invention may have a D(v,0.9) value at 3 months at 5-8° C. in the range from 0.5 μm to 10.0 μm. Preferably, in the range from 0.7 μm to 7.0 μm. More preferably, in the range from 1.0 μm to 4.0 μm. Most preferably, in the range from 2.4 μm to 3.1 μm.

The emulsion of the present invention therefore provides good particle size and particle size distribution a range desirable for syringeability at low concentration of the emulsifier. In addition, the emulsions of the present invention maintain the desired particle sizes and monomodal particle size distribution under storage over time.

The emulsions of the present invention, have a change in any or all of D(v,0.1), D(v,0.5), and D(v,0.9) between 0 hours and 15 days when kept at 37° C. of no more than 25%, preferably no more than 17%, most preferably no more than 12%.

The emulsions of the present invention, have a change in any or all of D(v,0.1), D(v,0.5), and D(v,0.9) between 0 hours and 1 month when kept at 5-8° C. 37° C. of no more than 25%, preferably no more than 17%, most preferably no more than 12%.

The emulsions of the present invention, have a change in any or all of D(v,0.1), D(v,0.5), and D(v,0.9) between 0 hours and 2 months when kept at 5-8° C. 37° C. of no more than 25%, preferably no more than 17%, most preferably no more than 12%.

The emulsions of the present invention, have a change in any or all of D(v,0.1), D(v,0.5), and D(v,0.9) between 0 hours and 3 months when kept at 5-8° C. 37° C. of no more than 30%, preferably no more than 25%, most preferably no more than 20%.

A feature of the present invention is that the desired levels of viscosity, stability, and particle size are obtained by low levels of emulsifier. The amount of emulsifier required per unit of water to be emulsified is particularly low for emulsifiers of the present invention.

The emulsifier can therefore have an emulsification efficiency value which represents the percentage weight of water emulsified per percentage weight of emulsifier. The emulsifier of the present invention may have an emulsification efficiency value greater than 15 in emulsions and vaccine formulations as defined herein. Preferably, greater than 20. More preferably, greater than 27. Most preferably, an emulsification efficiency value of greater than 30.

The vaccine comprises the emulsion system. It contains oil phase (generally mineral oil), water phase (containing proteins/antigen) and the emulsifier responsible to emulsify the oil and water and keep the emulsion stable.

The vaccine preparations based on emulsifier according to the invention can be prepared according to methods known in the art. The water in oil emulsions can be formed in to the vaccine formulation along with suitable antigens and other components. The antigen may be present in the water phase, and in the water as added to form the emulsion.

Typically, the vaccine formulations of the present invention comprises oil in the range from 20 wt. % to 90 wt. %. Preferably, 40% to 80%. Typically, the vaccine formulations of the present invention comprises water in the range from 80 wt. % to 10 wt. %. Preferably, 60% to 20%.

Typically, the vaccine formulations of the present invention comprises emulsifier in the range from 0.1 wt. % to 15 wt. %. Preferably, 0.1 wt. % to 10 wt. %.

Vaccination are used and administered in order to trigger the immune system and provide a protective immune response against an infectious agent. Vaccines may be based on living, attenuated microorganisms, or killed (inactivated) microorganisms, as well as on subunits of microorganisms as antigenic component.

The antigenic material may be mixed in the emulsion itself, or may be comprised in the formulation but not in the emulsion. The antigenic material may be mixed in water phase of the emulsion and vaccine formulation. In the vaccine the antigenic material may be present in the discontinuous water phase of the emulsion.

The emulsion and vaccine formulation of the present invention may be suitable for any strain or antigens that are used in water in oil emulsions. The emulsion and vaccine formulations may find particular use with strains and antigens for foot and mouth disease or Newcastle disease.

The emulsion and/or vaccine formulation may comprise surfactant, and these may be selected from non-ionic, anionic, cationic, amphoteric and/or zwitterionic surfactants.

The presence of saponin or aluminium hydroxide is common in vaccines that comprise excipients that present the property to induce the local immune response and act as adjuvants in the antibody production.

The vaccines according to the invention are preferably administered by parenteral methods, e.g. intramuscularly, subcutaneously, or intravenously. However if necessary the vaccines can also be administered by non-parental methods. The low viscosities of the emulsions used in the adjuvants and/or vaccines of the present invention are extremely suitable for parenteral administration, especially by injection.

All of the features described herein may be combined with any of the above aspects, in any combination.

In order that the present invention may be more readily understood, reference will now be made, by way of example, to the following description.

It will be understood that all tests and physical properties listed have been determined at atmospheric pressure and room temperature (i.e. 25° C.), unless otherwise stated herein, or unless otherwise stated in the referenced test methods and procedures.

Test methods for determining values are as follows:

Centrifugation—flask of 10 mL containing 10 g of the emulsion was centrifuged for 60 minutes at 4,000 rpm by a Baby Centrifuge.

Graduated Cylinder Check—50 mL of emulsion were tested over period of stability and the amount of oil released at the top was observed. It is generally acceptable for up to 10% of the volume added to be released in the top. Water in the bottom means that the emulsion had broken up and it is not acceptable.

Viscosity—A sample of 200 mL emulsion was tested using Brookfield DV-I. The formulation was evaluated from 100 rpm to 10 rpm. The formulations were evaluated using spindle S61 after 1 minute. The values of viscosity showed represent Montanide ISA 50 at 30 rpm and Emulsifier A at 60 rpm Particle Size—Measured using a Mastersizer 3000. Particle size analysis can predict emulsion stability over a period of time or when an application required a specific value. For injectable water in oil emulsion systems acceptable values are from 1 to 10 μm.

EMULSIFIER EXAMPLES

The following emulsifiers were prepared for testing in water in oil emulsion systems.

Example 1—Preparation of Emulsifier A

PEG-50 sorbitol (453 g, 31.2 wt. %) and poly-12-hydroxystearic acid (997 g, 68.8 wt. %) were charged in to a stainless steel reaction vessel. The mixture was heated to 210-220° C. under nitrogen spare and agitation. The reaction was held for 4-5 hours. The reaction was then cooled to 70-80° C. with the product (Emulsifier A) discharged.

Montanide ISA 50 & Emulsifier A—Composition and Formulation Process

Emulsifier A was formed in to low viscosity thin emulsion and high stable formulations for w/o systems. Emulsion systems using an existing emulsifier Montanide ISA 50 were also formed for comparison.

The following three emulsions were prepared:

Montanide 5% Emulsion—Montanide ISA 50, with w/o of 50 wt. % water and 50 wt. % oil (formed of 45 wt. % mineral oil and 5 wt. % mannide monoolate). Phosphate buffer system (PBS medium) pH 7.5 was used as water phase.

Montanide 1.5% Emulsion—Montanide ISA 50, with w/o of 50% water and 50 wt. % oil (formed of 48.5 wt. % mineral oil and 1.5 wt. % mannide monoolate). Phosphate buffer system (PBS medium) pH~7.5 was used as water phase.

Emulsifier A 1.5% Emulsion—Emulsifier A, with w/o of 50 wt. % water and 50 wt. % oil (formed of 48.5 wt. % mineral oil and 1.5 wt. % Emulsifier A). Phosphate buffer system (PBS medium) pH~7.5 was used as water phase. Three batches of this emulsion were made with the average of the results give.

Making the Emulsion

The emulsions were prepared using Silverson and normal grid for emulsions. The oil and emulsifier were added together in a beaker at a temperature less than 20° C. Under gentle agitation (1,000 rpm) the aqueous phase was added to the oil phase. The agitation was increased (4,000-7,000 rpm) to ensure homogeneity over 5 minutes.

Physical Properties

All samples were subjected to centrifugation, graduated cylinder check, viscosity, and particle size measurement. Results for a number of important physical properties of the emulsion as shown in Tables 1 to 3.

TABLE 1

Graduated Cylinder Check

| Conditions | Montanide 5% | Emulsifier A 1.5% |
| --- | --- | --- |
| 15 days at 37° C. | 1 mL layer at the top | 1 mL layer of turbid phase at the top, no creaming or phase separation |
| 1 month at 5-8° C. | 4 mL layer at the top | 1 mL layer of turbid phase at the top, no creaming or phase separation |
| 2 months at 5-8° C. | 5 mL layer at the top | 1 mL layer of turbid phase at the top, no creaming or phase separation |
| 3 months at 5-8° C. | 6 mL layer at the top | 1.5 mL layer of turbid phase at the top, no creaming or phase separation |

The Montanide emulsion showed a progressing increase of separated layer in the top of the emulsion achieving 6 mL of the layer. This is more than 10% of the volume and not acceptable. The emulsion with Emulsifier A formed a smaller layer in the top that did not progress until 2 months stability. The Montanide emulsion therefore showed phase separation, whilst the emulsion with Emulsifier A did not.

TABLE 2

Viscosity

| Conditions | Montanide 5% | Emulsifier A 1.5% |
| --- | --- | --- |
| 0 days | 141 cP | 71 cP |
| 15 days at 37° C. | 109 cP | 73 cP |
| 1 month at 5-8° C. | 138 cP | 81 cP |
| 2 months at 5-8° C. | 162 cP | 87 cP |
| 3 months at 5-8° C. | 158 cP | 83 cP |

The Montanide emulsion showed high viscosity and degradation of viscosity under storage. Emulsions with Emulsifier A showed a lower viscosity which allows for easier handling and syringeability, and the Montanide emulsion showed higher viscosity than emulsions with Emulsifier A at the same conditions of stability test.

TABLE 3

Particle Size

| | Montanide 5% | | | Emulsifier A 1.5% | | |
| --- | --- | --- | --- | --- | --- | --- |
| Conditions | D(v, 0.1) μm | D(v, 0.5) μm | D(v, 0.9) μm | D(v, 0.1) μm | D(v, 0.5) μm | D(v, 0.9) μm |
| 0 days* | 0.87 | 1.44 | 2.15 | 1.16 | 1.81 | 2.72 |
| 15 days at 37° C. | 0.82 | 1.30 | 2.07 | 1.10 | 1.73 | 2.62 |
| 1 month at 5-8° C. | 0.81 | 1.31 | 2.05 | 1.15 | 1.83 | 2.76 |

TABLE 3-continued

| | Particle Size | | | | | |
|---|---|---|---|---|---|---|
| | Montanide 5% | | | Emulsifier A 1.5% | | |
| Conditions | D(v, 0.1) μm | D(v, 0.5) μm | D(v, 0.9) μm | D(v, 0.1) μm | D(v, 0.5) μm | D(v, 0.9) μm |
| 2 months at 5-8° C. | 0.81 | 1.34 | 2.16 | 1.12 | 1.80 | 2.76 |
| 3 months at 5-8° C. | 0.99 | 1.78 | 3.05 | 0.97 | 1.66 | 2.67 |

*after formulation

The Montanide and Emulsifier A emulsion showed stable particle size over time during storage and monomodal particle size distribution. As Montanide ISA is presenting at 5% and Emulsifier A at 1.5% it should be considered that Emulsifier A is very effective on forming small internal phase particles and that the interfacial film formed is effective to keep the emulsion stable over the period of stability. Emulsions with Emulsifier A showed stable particle size over time during storage, and therefore a high degree of stability with little increase in large particles or aggregation leading to separation.

Comparison of Montanide 1.5% and Emulsifier a at 1.5%

The Montanide ISA 50 1.5% emulsion was compared against the Emulsifier A 1.5% emulsion. Results for a number of parameters were obtained as discussed above. Results for the Montanide emulsion are listed below, and can be compared to the Emulsifier A results shown in Tables 1-3.

Montanide 1.5% Results at 0 Days
Centrifugation—Not approved due to creaming
Viscosity—106 cP
Particle size D(v,0.9)—3.70 μm
Montanide 1.5% Results at 15 Days at 37° C.
Graduated cylinder—Not approved, emulsion breakage and water layer formed at bottom
Viscosity—sample broken so unmeasurable
Particle size D(v,0.9)—27.80 μm There are no results from the stability tests at 5° C.-8° C. as the formulation was not approved in the stress test 37° C.

Comparing the performance of the emulsions after 3 months it can be observed that the viscosities of emulsions with Emulsifier A at 1.5% are lower than Montanide ISA 50 at 1.5%. For injectable applications, and considering that it is a w/o system that can cause high local reaction, the lower is the value of viscosity the lower the local reaction may be. The values for Emulsifier A after 3 months were lower than Montanide ISA 50.

The particle size distribution for Emulsifier A was achieved whilst only using 1.5 wt. % of the emulsifier, when it is can be seen that 5% Montanide is required to achieve a comparable particle size distribution. Therefore, more than three time the amount of Montanide is required to achieve the same result, and Emulsifier A can be seen as being three time more effective per unit amount.

The results show Emulsifier A forms stable emulsions at levels of just 1.5 wt. %, provides lower viscosity emulsions which would therefore be easier to inject and have lower local reaction, and be easier to inject.

When preparing Montanide emulsions at 1.5% it was seen that it presented creaming after centrifugation at time zero which is an indication that are less stable. It was also seen that after 15 days the Montanide 1.5% emulsion had separated in two phases. This instable process is not acceptable for a w/o emulsion. Long term stability testing was therefore not possible since the emulsions phase separated.

The comparison of Montanide at 1.5% therefore shows that Emulsifier A can achieve stable emulsions at much lower levels than is achievable by prior emulsifiers.

It is to be understood that the invention is not to be limited to the details of the above embodiments, which are described by way of example only. Many variations are possible.

The invention claimed is:

1. A vaccine formulation comprising a water-in-oil emulsion and at least one vaccine antigen, oil, and water, where said emulsion comprises an emulsifier having a general structure (I):

$$R^1 \cdot [(AO)_n - R^2]_m \qquad (I)$$

wherein
R$^1$ is the residue of a polyol or polyamine, each said polyol or polyamine having m active hydrogen atoms, where m is an integer of at least 2;
AO is an oxyalkylene group;
each n independently represents an integer in the range from 1 to 100;
each R$^2$ independently represents hydrogen, or an acyl group represented by —C(O)R$^3$ wherein each R$^3$ independently represents a residue of Polyhydroxyalkyl carboxylic acid, polyhydroxyalkenyl carboxylic acid, hydroxyalkyl carboxylic acid, hydroxyalkenyl carboxylic acid, oligomer of hydroxyalkyl carboxylic acid, or oligomer of hydroxyalkenyl carboxylic acid; and
wherein on average at least two R$^2$ groups per molecule are alkanoyl groups as defined.

2. The formulation according to claim 1, wherein R$^1$ is the residue of a group having at least 3 free hydroxyl and/or amino groups.

3. The formulation according to claim 1, wherein R$^1$ is the residue of a sugar.

4. The formulation according to claim 1, where the emulsifier has a molecular weight of from 3,000 to 8,000.

5. The formulation according to claim 1, where the emulsifier has an HLB from 1.3 to 15.

6. The formulation according to claim 1, where the water-in-oil emulsion comprises 0.1 wt. % to 15 wt. % of the emulsifier.

7. The formulation according to claim 1, where the zero-shear viscosity of the emulsion at 0 days is less than 130 cP.

8. The formulation according to claim 1, where water particles present in emulsion have a D(v,0.5) value at 0 days in the range from 0.7 μm to 7.0 μm.

9. The formulation according to claim 1, where the emulsification efficiency value is greater than 15.

10. The formulation according to claim 3, wherein R$^1$ is the residue of a monosaccharide.

* * * * *